(12) United States Patent
Govari

(10) Patent No.: US 11,849,995 B2
(45) Date of Patent: Dec. 26, 2023

(54) DETECTION OF BALLOON CATHETER TISSUE CONTACT USING OPTICAL MEASUREMENT

(71) Applicant: Biosense Webster (Israel) Ltd., Yokneam (IL)

(72) Inventor: Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 201 days.

(21) Appl. No.: 17/179,254

(22) Filed: Feb. 18, 2021

(65) Prior Publication Data
US 2022/0257314 A1    Aug. 18, 2022

(51) Int. Cl.
*A61B 18/14*     (2006.01)
*A61B 18/00*     (2006.01)

(52) U.S. Cl.
CPC ........... *A61B 18/1492* (2013.01); *A61B 2018/00577* (2013.01); *A61B 2018/00982* (2013.01)

(58) Field of Classification Search
CPC ...... A61B 18/1492; A61B 2018/00577; A61B 2018/00982
See application file for complete search history.

(56) References Cited

U.S. PATENT DOCUMENTS

| | | | |
|---|---|---|---|
| 8,025,661 | B2 | 9/2011 | Arnold et al. |
| 8,456,182 | B2 | 6/2013 | Bar-Tal et al. |
| 10,136,945 | B2 | 11/2018 | Hettel |
| 10,682,179 | B2 | 6/2020 | Ransbury |
| 2005/0065504 | A1* | 3/2005 | Melsky ............... A61N 7/022 606/16 |
| 2005/0226548 | A1* | 10/2005 | Durkin ............... G01N 21/49 385/12 |
| 2007/0270792 | A1 | 11/2007 | Hennemann et al. |
| 2010/0041986 | A1* | 2/2010 | Nguyen ............ A61B 18/1492 606/33 |

(Continued)

FOREIGN PATENT DOCUMENTS

WO    WO-2011143468 A2 * 11/2011 ......... A61B 1/00082

OTHER PUBLICATIONS

Extended European Search Report dated Jul. 18, 2022, from corresponding European Application No. 22157169.8.

*Primary Examiner* — Linda C Dvorak
*Assistant Examiner* — Abigail Bock
(74) *Attorney, Agent, or Firm* — Troutman Pepper Hamilton Sanders LLP

(57) ABSTRACT

A medical system includes a catheter, a light source, a detector, a circulator, and a processor. The catheter includes a distal-end assembly for performing a medical operation on tissue in a cavity of an organ of a patient, the distal-end assembly including an optical fiber configured to guide transmitted light to interact with the tissue of the cavity, and to guide returned light that interacted with the tissue. The light source is configured to produce the transmitted light. The detector is configured to measure the returned light. The circulator is configured to couple the transmitted light from the light source to the optical fiber, and to couple the returned light from the optical fiber to the detector. The processor is configured to identify a contact of the distal-end assembly with the tissue based on the returned light measured by the detector, and to indicate the identified contact to a user.

15 Claims, 4 Drawing Sheets

(56) References Cited

U.S. PATENT DOCUMENTS

2015/0011896 A1\* 1/2015 Yelin ................... A61B 5/0075
 600/476
2016/0357007 A1\* 12/2016 Swanson ............ G01B 9/02028
2019/0374282 A1\* 12/2019 Tegg ...................... A61B 90/06

\* cited by examiner

DETECTION OF BALLOON CATHETER TISSUE CONTACT USING OPTICAL MEASUREMENT

FIELD OF THE INVENTION

The present invention relates generally to medical devices, and particularly to methods and systems for detecting contact between a catheter and tissue.

BACKGROUND OF THE INVENTION

Various techniques for verifying catheter contact with tissue were proposed in the patent literature. For example, U.S. Pat. No. 8,025,661 describes a cardiac ablation instrument that includes a catheter body and a tear-shaped balloon connected to the catheter body. The instrument further includes a radiant energy emitter that is axially movable within a central lumen of the catheter body. A radiant energy transparent body surrounds the energy emitter and includes a plurality of illumination fibers disposed circumferentially about the energy emitter. A detector communicates with a contact sensing element and is configured to determine an amount of at least one-color component of the reflected light. The amount of the at least one-color component being indicative of contact between the balloon and a target tissue site.

As another example, U.S. Pat. No. 10,136,945 describes devices and methods for providing and using an ablation catheter. The catheter may include an expandable member having a plurality of electrodes, where each electrode is in association with at least one contact sensor and at least one light emitting element. Light is emitted in response to the contact of the contact sensor with the tissue to be ablated. A light sensor disposed centrally to the catheter gathers light emitted from the light emitting elements and sends a signal to a system controller for display.

U.S. Pat. 10,682,179 describes ablation and visualization systems and methods to access quality of contact between a catheter and tissue. In some embodiments, a method for monitoring tissue ablation is provided, that comprises advancing a distal tip of an ablation catheter to a tissue in need of ablation; illuminating the tissue with UV light to excite NADH in the tissue, wherein the tissue is illuminated in a radial direction, an axial direction, or both; determining from a level of NADH fluorescence in the illuminated tissue when the distal tip of the catheter is in contact with the tissue; and delivering ablation energy to the tissue to form a lesion in the tissue.

SUMMARY OF THE INVENTION

An embodiment of the present invention that is described hereinafter provides a medical system including a catheter, a light source, a detector, a circulator, and a processor. The catheter includes a distal-end assembly for performing a medical operation on tissue in a cavity of an organ of a patient, the distal-end assembly including an optical fiber configured to guide transmitted light to interact with the tissue of the cavity, and to guide returned light that interacted with the tissue. The light source is configured to produce the transmitted light. The detector is configured to measure the returned light. The circulator is configured to couple the transmitted light from the light source to the optical fiber, and to couple the returned light from the optical fiber to the detector. The processor is configured to identify a contact of the distal-end assembly with the tissue based on the returned light measured by the detector, and to indicate the identified contact to a user.

In some embodiments, the processor is configured to identify the contact based on a change in measured intensity of the returned light.

In some embodiments, the processor is configured to establish a reference value for the intensity of the returned light while the distal-end assembly is not in contact with the tissue, and to identify the change relative to the reference value.

In an embodiment, a distal end of the fiber includes one of an optical diffusive element and an optical diffractive element, configured to couple the transmitted light from the fiber and couple the returned light that interacted with the tissue into the fiber.

In some embodiments, the optical diffractive element includes an optical grating coupler.

In other embodiments, the distal end of the fiber includes an opaque ending of the fiber. In yet other embodiments, the distal-end assembly includes an expandable transparent membrane.

In an embodiment, the transparent membrane includes multiple ablation electrodes disposed thereon, and wherein the processor is configured to output a recommendation to perform the medical operation with the electrodes based on identifying the contact with the tissue.

In some embodiments, the light source, the detector and the circulator are fitted at the distal-end assembly.

In some embodiments, the light source is a Light Emitting Diode (LED).

There is additionally provided, in accordance with another embodiment of the present invention, a method including inserting a distal-end assembly of a catheter into a cavity of an organ of a patient, for performing a medical operation on tissue in the cavity. Transmitted light is guided in an optical fiber inside the distal-end assembly, to interact with the tissue of the cavity. Returned light that interacted with the tissue is guided via the same optical fiber. A contact of the distal-end assembly with the tissue is identified based on the returned light measured by a detector, and the identified contact is indicated to a user.

The present invention will be more fully understood from the following detailed description of the embodiments thereof, taken together with the drawings in which:

DETAILED DESCRIPTION OF EMBODIMENTS

Overview

Figure 1:
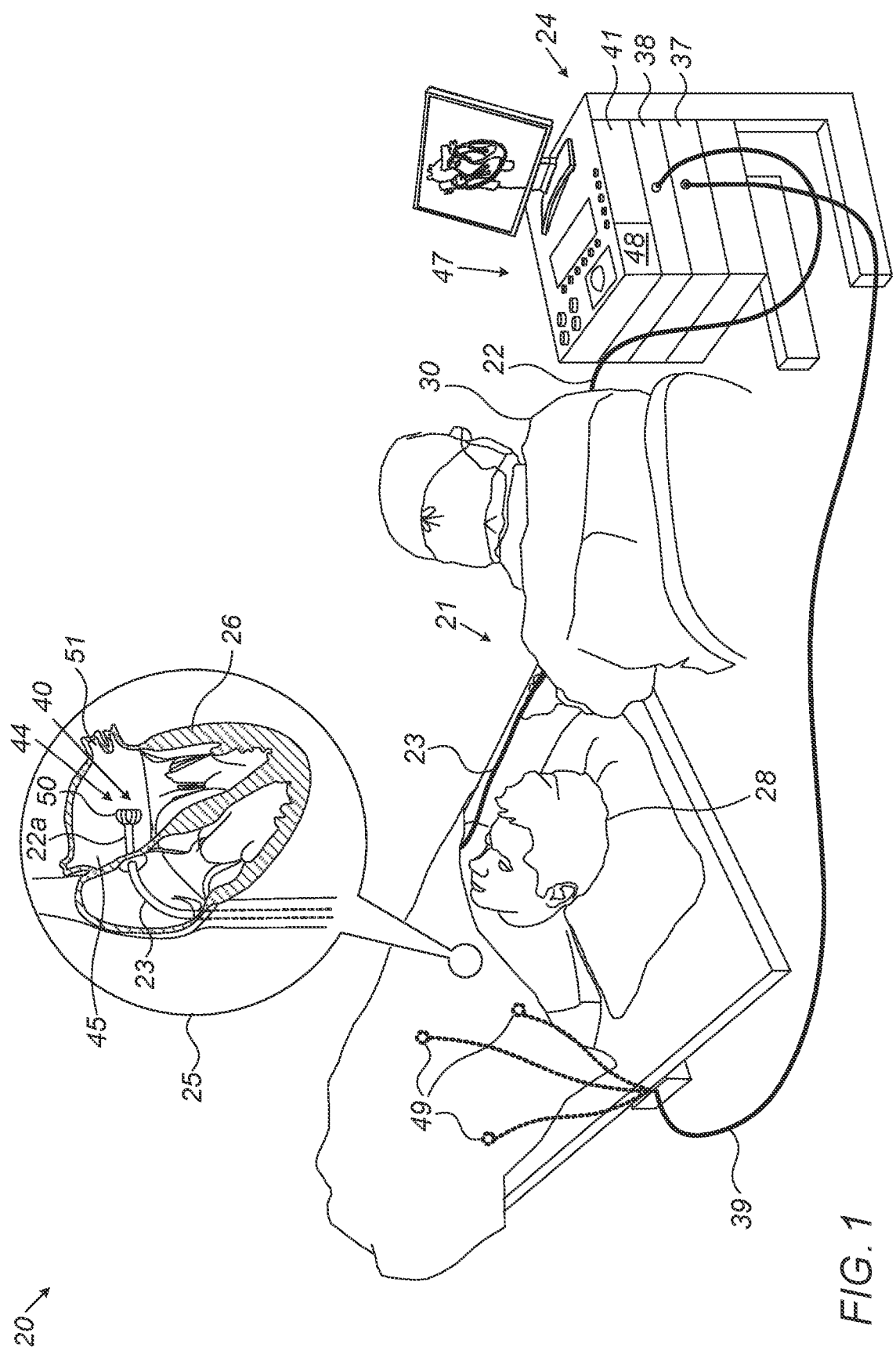
FIG. 1 is a schematic, pictorial illustration of a catheter-based diagnostics and/or ablation system comprising a transparent balloon catheter, in accordance with an embodiment of the present invention.

During a catheterization procedure of an organ of the body, such as cardiac electro-anatomical mapping and/or ablation, there may be a need to verify that electrodes disposed over an expandable membrane coupled to a distal end of a probe, such as a catheter, are in physical contact with wall tissue of a cavity of the organ, such as with a wall tissue of a cardiac chamber.

Embodiments of the present invention that are described hereinafter provide systems in which a distal-end assembly of a catheter includes means to emit light into surrounding media and collect light that interacts with the surrounding media, such as light reflected and/or scattered by a wall tissue of a cavity of the organ.

The disclosed techniques can be used with various distal-end assemblies. For example, the distal-end assembly may comprise an expandable frame, such as used in balloon and basket catheters, or comprise other frames, such as of basket, lasso, multi-arm, and tip catheters. In case of an expandable frame, the distal-end assembly may comprise a transparent expandable membrane (the remainder mostly covered by electrodes, e.g., of a balloon or a basket catheter).

In one embodiment, an optical fiber is installed in the expandable frame and used to transmit light from an external light source, such as a Light Emitting Diode (LED). The same optical fiber is used to convey returned light that interacts with a wall tissue of the cavity to an external detector (e.g., a photodiode). A distal end of the fiber, located inside the transparent expandable membrane of the distal end assembly, comprises a coupler, such as a grating coupler or a diffuser, configured to emit the transmitted light and to couple the returned light into the fiber.

An optical circulator is coupled at the proximal end of the optical fiber to separate the returned light from the transmitted light. The measurement from the detector (e.g., photodiode) is analyzed by a processor to indicate an occurrence of physical contact between the distal-end assembly and the tissue (e.g., by analyzing changes in the intensity of the returned light). The LED, the optical circulator, and the photodiode may be inside an external unit, also called hereinafter "contact detection module."

In another embodiment, the light source, the detector and the circulator are fitted at the distal-end assembly. For example, the LED, the circulator and the photodiode may all be located inside the transparent expandable membrane. In this embodiment, electrical signals are conveyed by a cable running in the catheter's shaft, to drive the LED and to convey measured electrical signals from the photodiode, in the opposite direction, to the processor.

In some embodiments, the processor initially measures the intensity of the returned light when the catheter is in the blood pool but prior to contact of the expanded membrane with tissue, therefore providing a reference value for the intensity. Since the intensity of the returned light changes when the transparent membrane contacts tissue relative to the reference value, the processor uses this change for contact detection.

In an embodiment, a system is provided that includes (a) a catheter, comprising a distal-end assembly for performing a medical operation on tissue in a cavity of an organ of a patient, the distal-end assembly comprising an optical fiber configured to guide transmitted light to interact with the tissue of the cavity, and to return returned light that interacted with the tissue, (b) a light source configured to produce the transmitted light, (c) a detector configured to measure the returned light, (d) a circulator configured to couple the transmitted light from the light source to the optical fiber, and to couple the returned light from the optical fiber to the detector, and (e) a processor, configured to identify a contact of the distal-end assembly with the tissue based on the returned light measured by the detector, and to indicate the identified contact to a user.

By offering a single optical-fiber-based tissue contact detection, a balloon catheter can be made with smaller diameter, allowing better flexibility of the shaft, and improved maneuverability, and therefore enable improved access to some target body locations.

System Description

FIG. 1 is a schematic, pictorial illustration of a catheter-based diagnostics and/or ablation system 20 comprising a transparent balloon catheter 40, in accordance with an embodiment of the present invention. System 20 comprises a catheter 21, wherein a shaft 22 of the catheter is inserted by a physician 30 through the vascular system of a patient 28 through a sheath 23. The physician then navigates a distal end 22a of shaft 22 to a target location inside a heart 26 of the patient.

In the embodiment described herein, catheter 21 may be used for any suitable diagnostic and/or therapeutic purpose, such as electrophysiological sensing and/or irreversible electroporation (IRE) and/or radiofrequency (RF) ablation to electro-physiologically isolate a PV ostium 51 tissue in left atrium 45 of heart 26.

Once distal end 22a of shaft 22 has reached the target location, physician 30 retracts sheath 23 and expands balloon 40, typically by pumping saline into balloon 40. Physician 30 then manipulates shaft 22 such that electrodes 50 disposed on the balloon 40 catheter engage an interior wall of a PV ostium 51 to perform electrophysiological sensing, and/or apply IRE and/or RF ablation via electrodes 50 to ostium 51 tissue.

Figure 2:
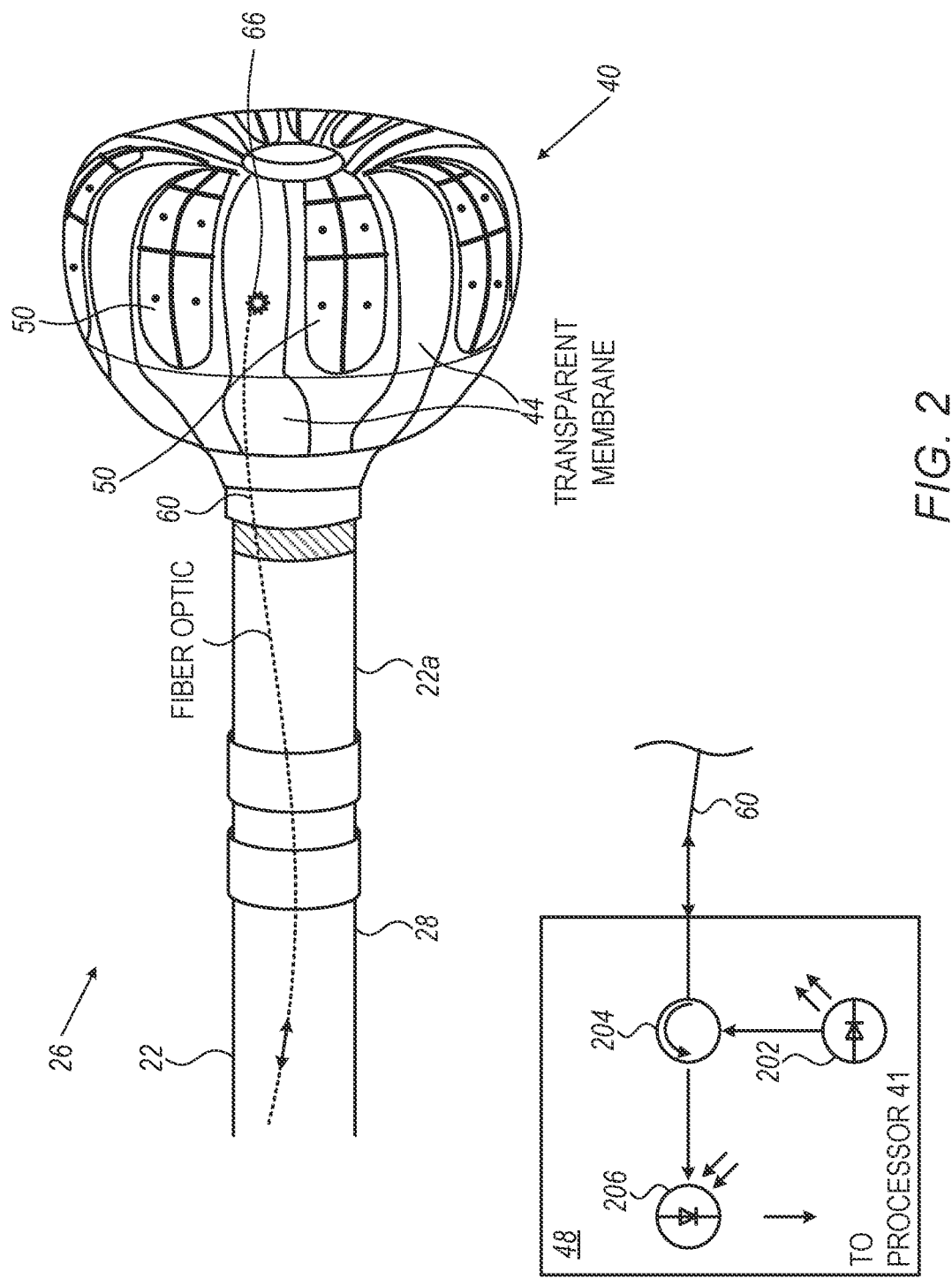
FIG. 2 is a schematic, pictorial illustration of the transparent balloon catheter and of the contact detection module of FIG. 1, in accordance with an embodiment of the invention.

As seen in inset 25, and in more detail in FIG. 2, expandable balloon 40 comprises multiple equidistant smooth-edge electrodes 50. A transparent membrane 44 of balloon 40 enables optical detection of contact with tissue, as described in FIG. 2. Due to the flattened shape of the distal portion of balloon 40, the distance between adjacent electrodes 50 remains approximately constant even where electrodes 50 cover the distal portion. Balloon 40 configuration, when used for IRE, therefore allows more effective electroporation (e.g., with approximately uniform electric field strength) between adjacent electrodes 50 while the smooth edges of electrodes 50 minimize unwanted thermal effects.

In the context of the present disclosure and in the claims, the term "approximately" for any numerical values or ranges indicates a suitable dimensional tolerance that allows the part or collection of components to function for its intended purpose as described herein.

The proximal end of catheter 21 is connected to a console 24 comprising an IRE pulse generator 38 configured to apply the IRE pulses between adjacent electrodes 50. The electrodes are connected to IRE pulse generator 38 by electrical wiring running in shaft 22 of catheter 21. An optical tissue-contact detection module 48 of console 24 is used with balloon 40, as described in FIG. 2.

An optical fiber (seen in FIG. 2) runs inside shaft 22 and is coupled at its proximal end to module 48. A distal end of the fiber includes a coupler (seen in FIG. 2) to emit the transmitted light and to couple the return light into the fiber.

Console 24 comprises a processor 41, typically a general-purpose computer, with suitable front end and interface circuits 37 for receiving signals from catheter 21 and from external electrodes 49, which are typically placed around the chest of patient 28. For this purpose, processor 41 is connected to external electrodes 49 by wires running through a cable 39.

During a procedure, system 20 can track the respective locations of electrodes 50 inside heart 26, using the Active Current Location (ACL) method, provided by Biosense-Webster (Irvine California), which is described in U.S. Pat. No. 8,456,182, whose disclosure is incorporated herein by reference.

In other embodiments, physician 30 can modify, from a user interface 47, any of the parameters, such as a wavelength, used by module 48. User interface 47 may comprise any suitable type of input device, e.g., a keyboard, a mouse, a trackball, among others.

Processor 41 is typically programmed in software to carry out the functions described herein, including analyzing signals acquired by module 48, to indicate an occurrence of membrane 44 contact with tissue. The software may be downloaded to the computer in electronic form, over a network, for example, or it may, alternatively or additionally, be provided and/or stored on non-transitory tangible media, such as magnetic, optical, or electronic memory.

In particular, processor 41 runs a dedicated algorithm as disclosed herein, including in FIG. 4, which enables processor 41 to perform the disclosed steps, as further described below.

Detecting Tissue Contact with a Balloon Catheter Using Optical Measurements

FIG. 2 is a schematic, pictorial illustration of transparent balloon catheter 40 and of the contact detection module 48 of FIG. 1, in accordance with an embodiment of the invention. The description below refers to balloon 40, but the techniques described below may be applied, mutatis mutandis, to any catheter having other types of expandable frames, such as, but not limited to, a basket catheter.

Balloon 40 comprises transparent membrane 44 with electrodes 50 disposed on the surface of membrane 44. In some embodiments, when placed in contact with tissue of heart 26, electrodes 50 are configured to sense intra-cardiac electrical signals from the tissue and/or to ablate tissue.

In some embodiments, electrodes 50 are configured to apply, to the tissue, ablation pulses received from IRE generator 38 and controlled by processor 41 and/or by physician 30, as described in FIG. 1 above.

In the shown embodiment, catheter 40 further comprises an optical fiber 60, which runs in shaft 22 and ends within the internal volume of balloon 40 with an optical coupler 66. Light emitted by coupler 66 propagates inside a saline solution used for inflating balloon 40 and interacts with media external to membrane 44, such as with blood and/or wall tissue (seen in FIG. 1).

The light emitted by coupler 66 is generated by an optical source (e.g., an LED) 202 inside unit 48, and transmitted to fiber 60 using a circulator 204. A return light is transmitted by circulator 204 to a photodetector 206. Using a circulator therefore provides separation of the incident light from the return light, which enables the detection of changes, even slight ones, in the intensity of the return light, due to physical contact of transparent membrane 44 with wall tissue.

Returned light measured by photodetector 206 are conveyed as an electrical signal to processor 41 for the processor to perform the analysis required to determine the occurrence of the membrane contact with wall tissue, as described above.

The configuration shown in FIG. 2 is provided by way of example. The principles described herein may similarly be applied to other types of ablation catheters, such as a basket-type distal end having a transparent membrane fitted to its expandable frame. Various types of couplers, such as those corrugated to emit in several directions, or having surface roughness to scatter light, may also be used.

A Balloon Catheter Using an Optical Grating Coupler

Figure 3:
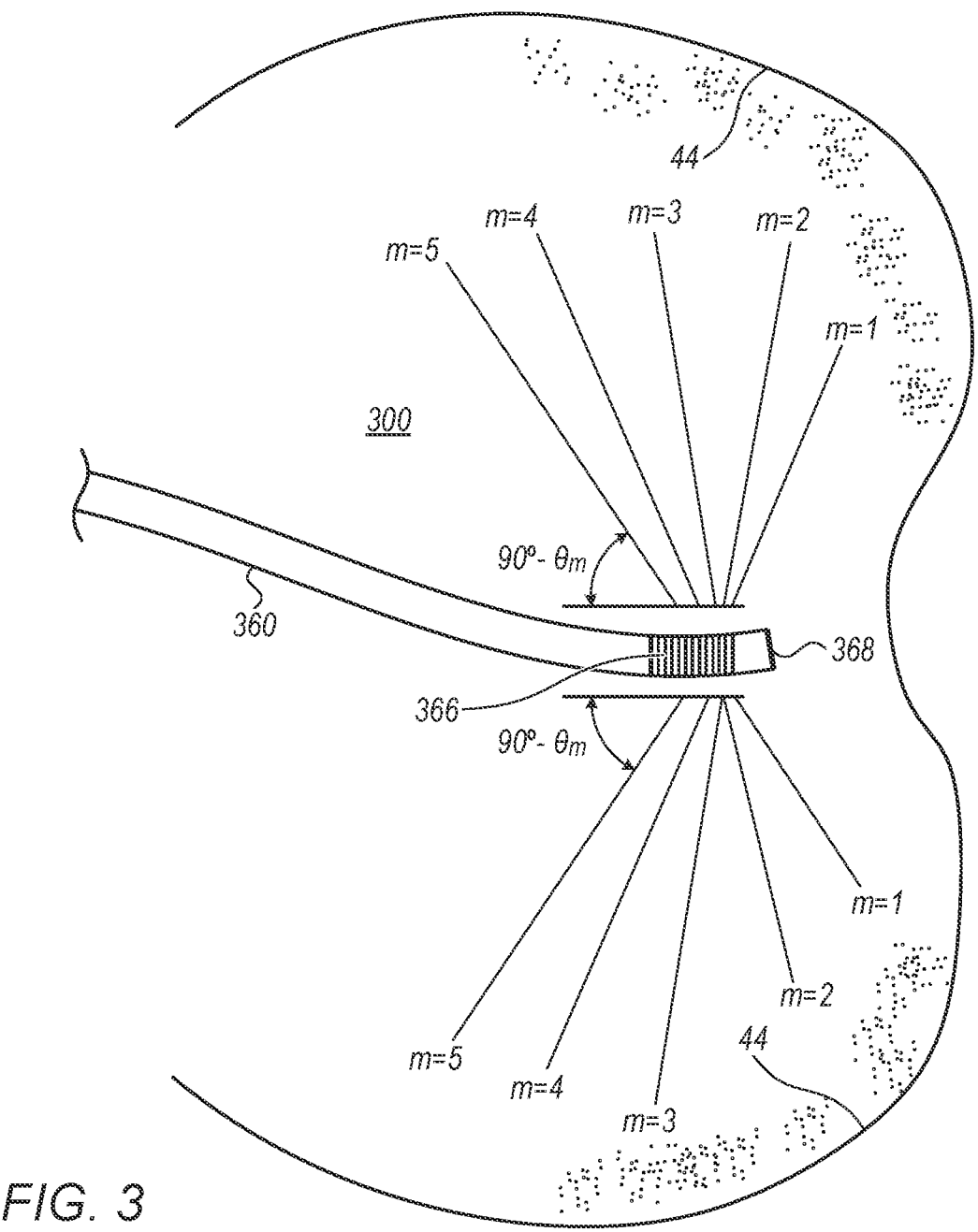
FIG. 3 is a schematic, pictorial illustration of a fiber grating coupler inside the transparent membrane of the balloon catheter of FIG. 1, in accordance with an embodiment of the invention.

FIG. 3 is a schematic, pictorial illustration of a fiber grating coupler 366 inside transparent membrane 44 of balloon catheter 40 of FIG. 1, in accordance with an embodiment of the invention. As seen, coupler 366 is patterned on optical fiber 360 at a distal end of fiber 360, with fiber 360 ending with an opaque termination, to minimize a reflected light.

Proper selection of coupler 366 parameters can make it highly efficient. Specifically, the coupling coefficient of the grating can be maximized by adjusting the groves and length of the grating. In this way, a substantial fraction (e.g., >30%) of the incident light intensity can be coupled out to interact with surrounding media.

Directions at which light is coupled by coupler 366 out into a surrounding media 300, and from which interacted light is coupled back into fiber 360, are defined with angles $\theta_m$ given by the grating equation:

$$\sin(\theta_m) = \frac{1}{n_0}\left(n_{\mathit{eff}} - \frac{m\lambda_0}{\Lambda}\right), m = 1, 2, 3 \ldots$$

where $n_0$ is the media refractive index (e.g., $n_0$ is approximately 1.33 for saline solution media), $n_{\mathit{eff}}$ is the effective refraction index (e.g., approximately 1.5) of the fiber guided light of peak intensity wavelength $\lambda_0$ (e.g., 630 nm red light), and $\Lambda$ is the period of the grating (e.g., several microns). Selecting $\Lambda \gg \lambda_0$ ensures that there are many diffraction orders that cover a wide area of the membrane. Alternatively, a smaller period $\Lambda$ (e.g., $\Lambda \geq \lambda_0$) may be selected, to cover, for example, with few diffraction orders, a selected perimeter strip of the membrane where contact determination is most important.

The configuration shown in FIG. 3 is provided by way of example. Other embodiments may induce more uniform emission of light over membrane 44 in other ways (e.g. a multiperiod grating or roughening).

Figure 4:
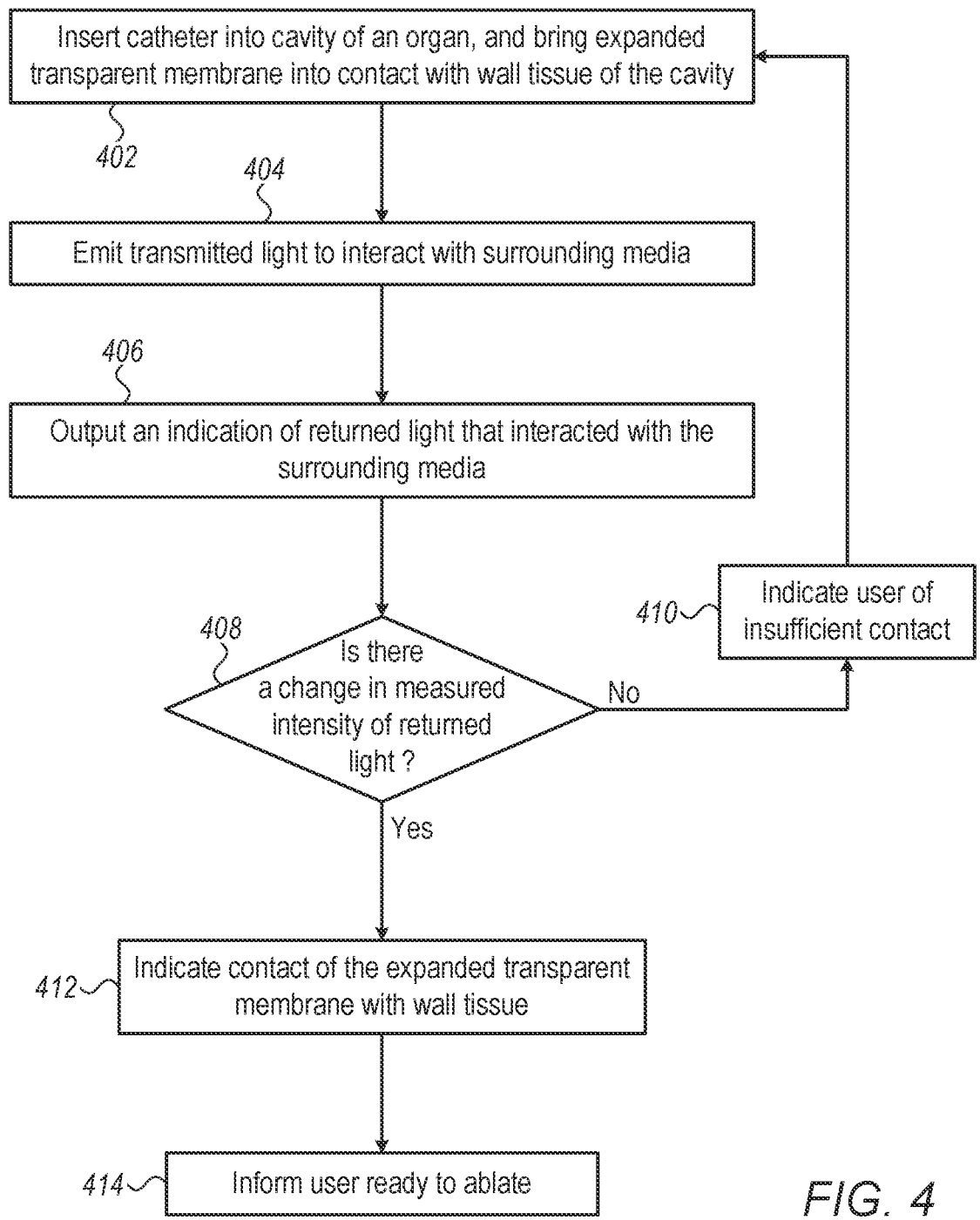
FIG. 4 is a flow chart that schematically illustrates a method for detecting tissue contact with the transparent balloon catheter of FIG. 1, in accordance with an embodiment of the present invention.

Method of Detecting Tissue Contact with a Balloon Catheter Using Optical Measurement FIG. 4 is a flow chart that schematically illustrates a method for detecting tissue contact with transparent balloon catheter 40 of FIG. 1, in accordance with an embodiment of the present invention. The algorithm, according to the presented embodiment, carries out a process that begins when physician 30 navigates balloon catheter 40 to a target tissue location in an organ of a patient, such as at PV ostium 51, using, for example, electrodes 50 as ACL sensing electrodes, and bringing membrane 44 of expanded balloon 40 into contact with ostium tissue, at catheter placement step 402.

In the process, unit 48 transmits light, which is emitted inside the cavity using coupler 360 (seen in FIG. 3), to interact with surrounding media, possibly including wall tissue in contact with membrane 44, at transmitted light emission step 404.

At an acquisition step 406, unit 48 acquires and measures a return light from surrounding media, possibly including wall tissue in contact with membrane 44.

At a checking step 408, processor 41 checks if a change of intensity of the return light occurred, e.g., to a degree indicative of a contact.

If the answer is no, the processor issues an indication of insufficient contact made with wall tissue (410), for example as a textual message on a display, and the process returns to step 402.

If the answer is yes, the processor issues an indication of a sufficient contact made with wall tissue (412). In an optional embodiment, the processor may further issue a notice that the balloon is in position for ablation (414).

Although the embodiments described herein mainly address cardiac applications, the methods and systems described herein can also be used in other medical applications, such as in neurology and otolaryngology.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A medical system, comprising:
a catheter, comprising a distal-end assembly for performing a medical operation on tissue in a cavity of an organ of a patient, the distal-end assembly comprising an optical fiber configured to guide transmitted light to interact with the tissue of the cavity, and to guide returned light that interacted with the tissue;
a light source configured to produce the transmitted light;
a detector configured to measure the returned light;
a circulator configured to couple the transmitted light from the light source to the optical fiber, and to couple the returned light from the optical fiber to the detector; and
a processor, configured to establish a reference value for an intensity of the returned light while the distal-end assembly is not in contact with the tissue and to identify a contact of the distal-end assembly with the tissue based on a change in the intensity of the returned light relative to the reference value.

2. The medical system according to claim 1, wherein the processor is configured to identify the contact based on a change in measured intensity of the returned light.

3. The medical system according to claim 1, wherein the light source, the detector and the circulator are fitted at the distal-end assembly.

4. The medical system according to claim 1, wherein the light source is a Light Emitting Diode (LED).

5. The medical system according to claim 1, wherein the processor is configured to measure an intensity.

6. The medical system according to claim 1, wherein a distal end of the fiber comprises one of an optical diffusive element and an optical diffractive element, configured to couple the transmitted light from the fiber and couple the returned light that interacted with the tissue into the fiber.

7. The medical system according to claim 6, wherein the distal end of the fiber comprises an opaque ending of the fiber.

8. The medical system according to claim 6, wherein the optical diffractive element comprises an optical grating coupler.

9. The medical system according to claim 8, wherein a distal end of the optical fiber, comprising the optical grating coupler, is disposed inside an expandable transparent membrane.

10. The medical system according to claim 1, wherein the distal-end assembly comprises an expandable transparent membrane.

11. The medical system according to claim 10, wherein the transparent membrane comprises multiple ablation electrodes disposed thereon, and wherein the processor is configured to output a recommendation to perform the medical operation with the electrodes based on identifying the contact with the tissue.

12. The medical system according to claim 10, wherein the light source, the detector, and the circulator are each disposed inside the expandable transparent membrane.

13. A method, comprising:
inserting a distal-end assembly of a catheter into a cavity of an organ of a patient, for performing a medical operation on tissue in the cavity;
guiding transmitted light in an optical fiber inside the distal-end assembly, to interact with the tissue of the cavity;
guiding via the same optical fiber returned light that interacted with the tissue;
establishing a reference value for an intensity of the returned light while the distal-end assembly is not in contact with the tissue; and
identifying a contact of the distal-end assembly with the tissue based on a change in the intensity of the returned light measured by a detector relative to the reference value, and
indicating the identified contact to a user.

14. The method according to claim 13, wherein identifying the contact comprises identifying a change in measured intensity of the returned light.

15. The method according to claim 13, further comprising coupling the transmitted light from a distal end of the fiber, and coupling the returned light that interacted with the tissue into the distal end of the fiber, using one of an optical diffusive element and an optical diffractive element.

* * * * *